United States Patent [19]

Kousai et al.

[11] Patent Number: 4,747,833
[45] Date of Patent: May 31, 1988

[54] MEDICAL INSTRUMENT-GUIDING TUBE AND ASSEMBLY COMPRISING THE SAME

[75] Inventors: Tadashi Kousai; Yousuke Moriuchi, both of Fujinomiya, Japan

[73] Assignee: Terumo Kabushiki Kaisha, Tokyo, Japan

[21] Appl. No.: 921,379

[22] Filed: Oct. 22, 1986

[30] Foreign Application Priority Data

Oct. 28, 1985 [JP] Japan .................................. 60-240984

[51] Int. Cl.$^4$ .............................................. A61M 5/00
[52] U.S. Cl. .................................... 604/164; 604/161; 604/280
[58] Field of Search .............................. 604/164–170, 604/158–161, 280

[56] References Cited

U.S. PATENT DOCUMENTS

| 3,656,479 | 4/1972 | Huggins | 604/161 |
| 3,713,442 | 1/1973 | Walter | 604/161 |
| 4,054,136 | 10/1977 | Von Zeppelin | 604/160 |
| 4,402,685 | 9/1983 | Buhler et al. | 604/280 |
| 4,451,256 | 5/1984 | Weikl et al. | 604/164 |

Primary Examiner—Dalton L. Truluck
Attorney, Agent, or Firm—Burns, Doane, Swecker & Mathis

[57] ABSTRACT

A medical instrument-guiding tube for guiding a catheter or other rod-like medical instrument into a blood vessel. This guiding tube comprises a hollow tube body and at least one linear body integrally joined to the tube body along the longitudinal direction of the tube body. The plastic resin forming the tube body has a poor compatibility with that of linear body. The tube body and the linear body are engaged together through a complementary concave-convex engagement which can be disengaged with a reasonable force.

6 Claims, 3 Drawing Sheets

F I G. 10
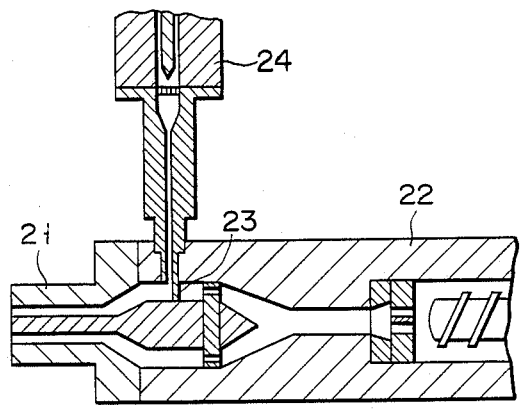
F I G. 11
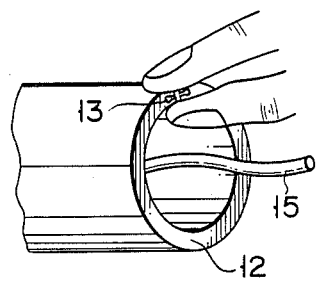
F I G. 12
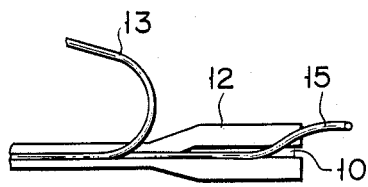

MEDICAL INSTRUMENT-GUIDING TUBE AND ASSEMBLY COMPRISING THE SAME

BACKGROUND OF THE INVENTION

1. Field of the Invention

The present invention relates to a flexible synthetic resin tube for guiding a rod-like medical instrument such as a catheter or guide wire into a blood vessel to keep the rod-like medical instrument attached to the blood vessel.

2. Description of the Prior Art

A flexible synthetic resin tube is generally used for guiding, for example, a catheter into a blood vessel to keep the catheter attached to the blood vessel. As shown in FIG. 1, a syringe 2 is mounted to a guiding tube 1 such that the tip of the inner needle 3 of the syringe 2 projects through the distal end of the guiding tube 1. Then, the inner needle 3 is inserted into a blood vessel 4 until the distal end of the guiding tube 1 is positioned within the blood vessel 4. Further, the inner needle 3 is withdrawn from the blood vessel 4, with the guiding tube 1 left attached to the blood vessel 4, as shown in FIG. 2. In this condition, a catheter 5 is inserted through the guiding tube 1 such that the distal end portion of the catheter 5 is positioned within the blood vessel 4, as shown in FIG. 3. After the distal end portion of the catheter 5 is held within the blood vessel 4 as desired, it is desirable to withdraw the guiding tube 1 from the blood vessel 4 and from the catheter 5. It is undesirable from sanitary and operational view points to leave the guiding tube 1, which is no more useful, attached to the catheter 5.

However, it is impossible to withdraw the guiding tube 1 from the catheter 5 as the catheter 5 has an enlarged portion such as connector 6.

Under the circumstances, measures have been proposed for removing the guiding tube 1 from the catheter 5 after insertion of the distal end portion of the catheter 5 into the blood vessel 4. For example, it has been proposed to form in advance a slit in the guiding tube, in the longitudinal direction thereof, so as to remove the used guiding tube from the catheter along the slit. However, the slit may expand when the catheter is guided into the blood vessel causing leakage of the blood through the slit. To prevent the problem, the width of the slit must be restricted, making it difficult to remove the used guiding tube from the catheter.

U.S. Pat. No. 4,402,685 teaches that the guiding tube is provided with a pair of linear bodies facing each other in the radial direction of the tube and extending in the longitudinal direction of the tube. The linear bodies are formed of a plastic material which is heterogeneous from the plastic material forming the other part of the guiding tube. The proximal end portion of the guiding tube is inflated to provide the mounting part for the inner needle hub. The mounting part is provided with slits connected to the linear bodies. The guiding tube after use is split along the linear bodies by pulling the mounting part in opposite directions to split the slits. However, the linear bodies tend to crack during after-treatments such as cutting of the guiding tube or when the product guiding tube is handled, leading to uselessness or other serious problems such as blood leakage.

SUMMARY OF THE INVENTION

The present invention is intended to provide a medical instrument-guiding tube free from damages such as cracking during after-treatment or handling of the tube. The guiding tube, after use, can be easily removed from the medical instrument, e.g., a catheter.

According to the present invention, there is provided a medical instrument-guiding tube for guiding a rod-like medical instrument, comprising a hollow tube body and at least one linear body extending in the longitudinal direction of the tube body which is integrally and water-tight joined to the tube body, the tube body and the linear body being formed of synthetic resins poorly compatible with each other, having complementary concave-convex engaging portions for water-tight engagement between the tube body and the linear body, where the linear body is capable of peeling from the engaging portion with reasonable force.

It may be advisable, as required, to form a thin film of the tube body thermoplastic synthetic resin on the upper or lower surface of the linear body. The film, if formed, should desirably be about 0.05 to 0.3 mm thick.

The present invention also provides a medical instrument-guiding assembly, comprising a medical instrument-guiding tube, for guiding a rod-like medical instrument. Said guiding tube has a hollow tube body and at least one linear body extending in the longitudinal direction of the tube body which is integrally and water-tight water-tightly joined to the tube body. The tube body and the linear body are formed of synthetic resins poorly compatible with each other and have complementary concave-convex engaging portions for the water-tight engagement between the tube body where and the linear body, the linear body is capable of peeling from the engaging portion with a reasonable force.

An inner needle is provided with hub hub engaging with the proximal end portion of the guiding tube and which is detachably insertable into the guiding tube. The blade tip portion of the inner needle projects through the distal end of the guiding tube.

BRIEF DESCRIPTION OF THE DRAWINGS

FIG. 10 is a cross sectional view showing as an example an apparatus for manufacturing a medical instrument-guiding tube of the present invention; and FIGS. 11 and 12 are oblique views showing how to peel the linear body from the tube body.

DESCRIPTION OF THE PREFERRED EMBODIMENTS

Figure 1:
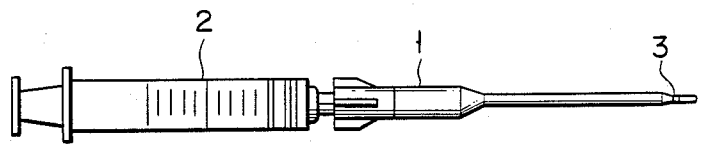
FIGS. 1 to 3 schematically show how to use a medical instrument-guiding tube.

The present invention will now be described in detail, with reference to FIGS. 4 to 12. As seen from FIG. 4, which is a side view, a medical instrument-guiding tube 11 of the present invention comprises a hollow tube body 12 formed of a first thermoplastic synthetic resin and a linear body 13 formed of a second thermoplastic synthetic resin. The linear body 13 is embedded in a slit 10 extending in the longitudinal direction of the tube body 12, as seen from FIGS. 5 or 7. The linear body 13, which extends through both the small and large diameter portions of the tube body 12, is formed in a single extrusion step. As seen from FIG. 6, it is possible to provide a plurality of linear bodies facing each other in the radial direction of the tube body. As is apparent from FIG. 7, the linear body 13 laterally projects right and left in substantially the central thick portion of the linear body 13. As a result, a complementary concave-convex engagement is achieved between the tube body 12 and the linear body 13 increasing the contact area between the two. It follows that the engagement between the tube body 12 and the linear body 13 is strengthened. The engagement can be further strengthened, if a thick engaging part 13a is formed at the tip of the widened part of the linear body, as shown in the drawings.

It is possible to appropriately select the first thermoplastic synthetic resin forming the tube body 12. In general, it is advisable to use an olefinic polymer, which may or may not be modified, such as polyethylene, fluorinated ethylene-propylene copolymer, tetrafluoroethylene polymer, or ethylene-tetrafluoroethylene copolymer.

It is also possible to appropriately select the second thermoplastic synthetic resin forming the linear body the second resin should be poorly compatible with the first thermoplastic synthetic resin and should have a melt viscosity which permits the second resin to be molded together with the first resin. Concerning the compatibility noted above, the linear body should be capable of being manually peeled off when the guiding tube is removed, but should not be readily peeled from the tube body before use of the guiding tube. The second resin generally used in the present invention includes, for example, polyvinylchloride, polyurethane, polyethylene terephthalate and polyamide.

The width W (see FIG. 7) and the length of the lateral projection of the linear body 13 may be appropriately determined in view of the desired width of the slit 10, the peeling capability of the linear body 13 and the bonding strength between the tube body 12 and the linear body 13.

Figure 8:
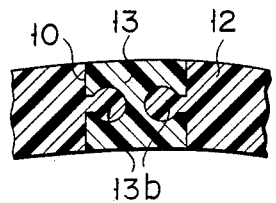

FIG. 8 shows a modification of the cross sectional shape of the linear body 13. In this modification, the linear body 13 is "I"-shaped in cross section, i.e., the linear body 13 is wide and shrunk in the central part to provide lateral projections 13b of the tube body 12. In the present invention, the shape of the complementary concave-convex engaging part is not restricted to those shown in the drawings as long as the shape of the engaging part is adapted to ensure a sufficient engagement between the linear body and the tube body.

Figure 9:
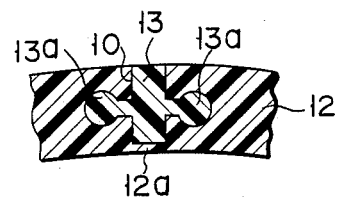

FIG. 9 shows another modification. In this case, the lower surface of the linear body 13 is covered with a thin film 12a of the first thermoplastic synthetic resin constituting the tube body 12 so as to improve the engaging strength between the linear body 13 and the tube body 12. Of course, the thin film noted above may also be formed on the upper surface of the linear body 13, with the same effect. The film 12a should be able to be broken in the step of peeling the linear body 13 and, thus, should not be unduly thick. Generally, the thickness of the film 12a should be 0.3 mm or less, desirably, about 0.05 to 0.3 mm.

Figure 4:
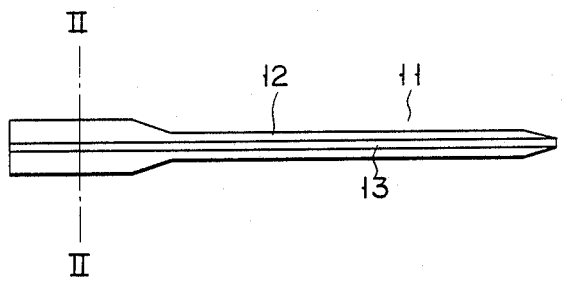
FIG. 4 is a side view showing a medical instrument-guiding tube according to one embodiment of the present invention.
Figure 5:
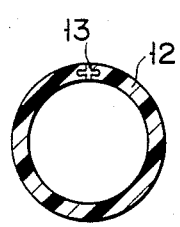
FIGS. 5 and 6 are cross sectional views along line V—V of FIG. 4.
Figure 6:
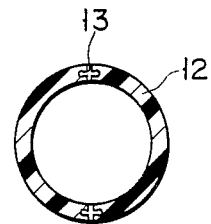
Figure 7:
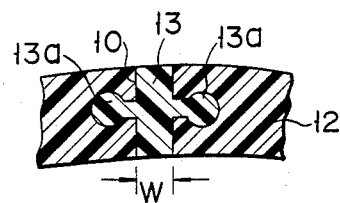
FIGS. 7 to 9 are cross sectional views showing in a magnified fashion modifications of the linear body portion included in the medical instrument-guiding tube of the present invention.

The medical instrument-guiding tube 11 is manufactured by using, for example, an extruder as is shown in FIG. 10. As can be seen from the drawing, the extruder comprises a first extruding section 22 having an annular die 21 formed at the tip and a second extruding section 24 provided with a nozzle 23 open in the molten resin passageway upstream of the die 21. A guiding tube having the linear body 13 embedded in the slit of the tube body 12, as shown in FIG. 4, is extruded through the die 21, if the first and second extruding sections 22 and 24 are operated simultaneously. The cross sectional shape of the linear body 13 corresponds to the cross sectional shape in the outlet opening of the nozzle 23 and, thus, can be optionally selected as desired.

Figure 2:
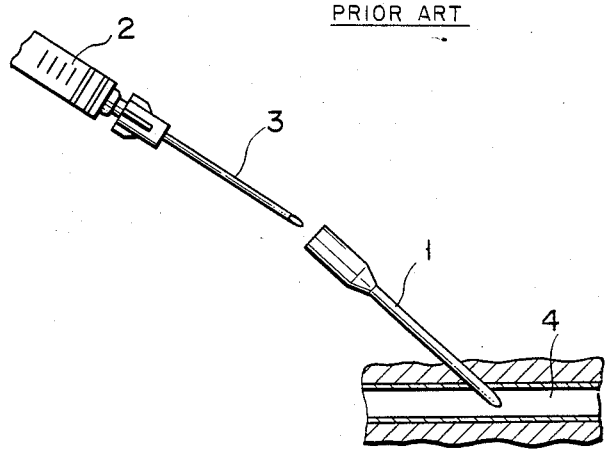
Figure 3:
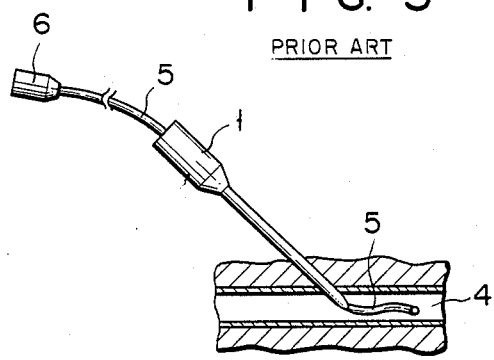

The medical instrument-guiding tube of the present invention is used as follows. In the first step, the guiding tube is used for guiding, for example, a catheter into a blood vessel as shown in FIGS. 1-3. To be more specific, a syringe as shown in FIG. 1 is mounted to the tube 11. The distal end portion of the tube 11 is inserted into the blood vessel together with the inner needle of the syringe, followed by withdrawing the inner needle so as to secure the distal end portion of the guiding tube 11 within the blood vessel. Then, the catheter is inserted through the guiding tube 11 into the blood vessel.

After the insertion, the guiding tube 11 is removed from the catheter. In removing the guiding tube 11, the linear body 13, which is positioned to face upward, is manually held as shown in FIG. 11 and, then, pulled upward as shown in FIG. 12 so as to peel the linear body 13 from the slit 10 of the tube body 12. It follows that the slit 10 readily permits the guiding tube 11 to be removed from the catheter 15.

In the embodiment described above, the medical instrument-gyiding tube is used for guiding a catheter. However, it is apparent from the technical idea of the present invention that the guiding tube can be used for guiding not only a catheter but also any kind of rod-like medical instrument.

As described above in detail, the medical instrument-guiding tube of the present invention comprises a tube body formed of a thermoplastic material and provided with a slit extending in the longitudinal direction and a linear body embedded in the slit. The linear body is formed of a thermoplastic material heterogeneous from and poorly compatible with the resin forming the tube body. It follows that the linear body is unlikely to peel from the tube body during after-treatments such as cutting of the guiding tube or when the product tube is handled. Naturally, blood leakage can be prevented when, for example, a catheter is inserted through the guiding tube into a blood vessel. It should also be noted that the width of the linear body can be optionally determined as desired, making it possible to easily remove the guiding tube from the medical instrument attached to a blood vessel. What should also be noted is that the guiding tube can be manufactured by, for example, an extruder such that the proximal end portion of the guiding tube is capable of engagement with the inner needle hub. Naturally, it is unnecessary to provide a separate member for engagement of the guiding tube with the inner needle hub. In addition, the guiding tube can be manufactured at a low cost.

What is claimed is:

1. A medical instrument-guiding tube for guiding a rod-like medical instrument, comprising a hollow tube body having a cutaway section extending in the longitudinal direction of the tube body and at least one linear body extending in the longitudinal direction of the tube body in such a manner as to fill the cutaway section and integrally and water-tightly joined to the tube body, the tube body and the linear body are formed of synthetic resins poorly compatible with each other, having a complementary concave-convex engaging portion for the water-tight engagement between the tube body and the linear body, the upper or lower surface of the linear body being covered with a thin film of the thermoplastic resin forming the tube body, wherein the linear body is capable of peeling from the engaging portion with the use of reasonable force.

2. A medical instrument-guiding tube according to claim 1, wherein the film covering the upper or lower surface of the linear body is 0.05 to 0.3 mm thick.

3. A medical instrument-guiding tube according to claim 1, wherein the linear body is "+"-shaped in its cross section.

4. A medical instrument-guiding tube according to claim 1, wherein the linear body is substantially "I"-shaped in its cross section.

5. A medical instrument-guiding tube according to claim 1, which comprises two linear bodies provided parallel with and apart from each other.

6. A medical instrument-guiding assembly, comprising a medical instrument-guiding tube for guiding a rod-like medical instrument, said guiding tube including a hollow tube body, having a cutaway section extending in the longitudinal direction of the tube body, and at least one linear body extending in the longitudinal direction of the tube body in such a manner as to fill the cutaway section and integrally joined water-tight to the tube body, the upper or lower surfaces of the linear body being covered with a thin film of the thermoplastic resin forming the tube body, the tube body and the linear body being formed of synthetic resins poorly compatible with each other, having a complementary concave-convex engaging portion for the water-tight engagement between the tube body and the linear body, and the linear body being capable of peeling from the engaging portion with a reasonable force; and an inner needle provided with a hub engaged with the proximal end of the guiding tube and detachably inserted into the guiding tube, the blade tip portion of the inner needle projecting through the distal end of the guiding tube.

* * * * *

UNITED STATES PATENT AND TRADEMARK OFFICE
CERTIFICATE OF CORRECTION

PATENT NO. : 4,747,833
DATED : May 31, 1988
INVENTOR(S) : Kousai et al

It is certified that error appears in the above-identified patent and that said Letters Patent is hereby corrected as shown below:

Column 1, line 32, amend "more" to -- longer --.

Signed and Sealed this

Seventeenth Day of January, 1989

*Attest:*

DONALD J. QUIGG

*Attesting Officer*    *Commissioner of Patents and Trademarks*